(12) United States Patent
Beardall et al.

(10) Patent No.: US 9,084,665 B2
(45) Date of Patent: Jul. 21, 2015

(54) SYSTEMS AND METHODS FOR PROVIDING A THERMO-ELECTRO-STIMULATION PROBE DEVICE

(71) Applicants: Larry K. Beardall, Sandy, UT (US); Ian K. Brown, Midvale, UT (US); Scott R. Mabey, Bountiful, UT (US); William R. Lindhardt, West Jordan, UT (US); Douglas G. Sampson, Salt Lake City, UT (US)

(72) Inventors: Larry K. Beardall, Sandy, UT (US); Ian K. Brown, Midvale, UT (US); Scott R. Mabey, Bountiful, UT (US); William R. Lindhardt, West Jordan, UT (US); Douglas G. Sampson, Salt Lake City, UT (US)

(73) Assignee: DYNATRONICS CORPORATION, Salt Lake City, UT (US)

( * ) Notice: Subject to any disclaimer, the term of this patent is extended or adjusted under 35 U.S.C. 154(b) by 0 days.

(21) Appl. No.: 13/776,483

(22) Filed: Feb. 25, 2013

(65) Prior Publication Data
US 2013/0238043 A1 Sep. 12, 2013

Related U.S. Application Data

(60) Provisional application No. 61/602,393, filed on Feb. 23, 2012.

(51) Int. Cl.
| | |
|---|---|
| *A61N 1/05* | (2006.01) |
| *A61F 7/00* | (2006.01) |
| *A61N 1/32* | (2006.01) |
| *A61F 7/02* | (2006.01) |
| *A61N 5/06* | (2006.01) |

(52) U.S. Cl.
CPC . *A61F 7/007* (2013.01); *A61N 1/32* (2013.01); *A61F 2007/0054* (2013.01); *A61F 2007/0075* (2013.01); *A61F 2007/0078* (2013.01); *A61F 2007/0296* (2013.01); *A61N 2005/0644* (2013.01)

(58) Field of Classification Search
CPC ............................ A61N 1/0452; A61N 1/0456
USPC .................................................. 607/3, 96–98
See application file for complete search history.

(56) References Cited

U.S. PATENT DOCUMENTS

| | | | | |
|---|---|---|---|---|
| 4,082,089 | A  * | 4/1978 | Moriyama et al. | 601/19 |
| 5,097,828 | A  * | 3/1992 | Deutsch | 607/104 |
| 6,210,355 | B1 * | 4/2001 | Edwards et al. | 604/22 |
| 6,567,696 | B2 * | 5/2003 | Voznesensky et al. | 607/3 |
| 2003/0216728 | A1 * | 11/2003 | Stern et al. | 606/41 |
| 2011/0230701 | A1 * | 9/2011 | Simon et al. | 600/9 |

* cited by examiner

*Primary Examiner* — Paula J Stice
(74) *Attorney, Agent, or Firm* — David B. Tingey; Bryant J. Keller; Kirton McConkie (57) ABSTRACT

A hand-held probe device capable of providing electro-stimulation and thermo-stimulation to a patient is described herein. While the probe device can include any suitable component, in some instances, it includes a probe head made with an electrically and thermally-conductive material. In some instances, the probe device also includes a temperature control mechanism that is configured to raise and lower a temperature of the probe head. The probe head is also connectable to an electro-stimulation unit (such as a transcutaneous electrical nerve stimulation unit) such that the probe head is able to provide electro-stimulation simultaneously with thermo-stimulation. Although the temperature control mechanism can include any suitable component, in some instances, it includes a thermoelectric device, such as a Peltier circuit. Other implementations are also described.

22 Claims, 10 Drawing Sheets

FIG. 9

SYSTEMS AND METHODS FOR PROVIDING A THERMO-ELECTRO-STIMULATION PROBE DEVICE

CROSS-REFERENCE TO RELATED APPLICATION

This application claims priority to U.S. Provisional Patent Application Ser. No. 61/602,393, filed Feb. 23, 2012, and entitled "THERMOELECTRIC PROBE DEVICE;" the entire disclosure of which is hereby incorporated by reference.

BACKGROUND OF THE INVENTION

1. Field of the Invention

The present invention relates generally to a thermo-electro-stimulation probe device that is capable of applying heating, cooling, and/or applying electrical current and/or stimulation to a patient as part of a thermo-electrotherapy treatment.

2. Background and Related Art

Transcutaneous electrical stimulation ("TES") is a relatively non-invasive technique that is used by many healthcare providers across the world. In some cases, TES is used to stimulate nerves in a process referred to as transcutaneous electrical nerve stimulation ("TENS"). In this regard, TENS often uses an electrical current to stimulate peripheral nerve ends and/or acupuncture points across the surface of a patient's skin. While this stimulation may cause several effects, in some cases, it has been found to provide analgesic effects by activating specific natural pain relief mechanisms.

As a result of its simplicity, TENS can be administered either in clinics by healthcare professionals, or at home by patients. In some cases, the ease of use, general safety, portability, and effectiveness of TENS equipment make TENS a preferred treatment, oftentimes more favorable than the long-term use of medications and nerve blocks for chronic pain. In this regard, in addition to being relatively non-invasive, TENS treatments may also have relatively few side effects when compared with certain competing types of drug therapy.

Although TENS treatments have been found to be useful in a variety of applications (including for providing analgesic effects, increasing blood flow to a treated area, etc.), some conventional TENS equipment may have shortcomings. By way of example, as some TENS electrodes are strapped or adhered to patients, and as some such electrodes are fixed to devices that limit the electrodes' movement, such electrodes may not be effectively used to manually massage a patient while the patient receives a TENS treatment. In another example, the electrodes of many TENS units are configured to stimulate a patient through a TENS treatment, but are not configured to provide the patient with other useful types of stimulation.

Thus, although methods currently exist for treating a patient with TENS, challenges still exist. Accordingly, it would be an improvement in the art to augment or even replace current techniques with other techniques.

BRIEF SUMMARY OF THE INVENTION

The present invention relates generally to a thermo-electro-stimulation probe device that is capable of applying heating, cooling, and/or applying electrical current and/or stimulation to a patient as part of a thermo-electrotherapy treatment.

Some implementations of the present invention comprise a hand-held probe device that is capable of providing electro-stimulation (or a treatment in which electricity is applied to a patient) and thermo-stimulation (or a treatment in which a portion of a patient is heated or cooled). While the probe device can include any suitable component, in some instances, it includes a probe head made with an electrically and thermally conductive material. Additionally, in some instances, the probe device also includes (or is otherwise connected to) a temperature control mechanism that is configured to raise and lower a temperature of the probe head. Moreover, in order to provide electro-stimulation, the probe head is connected to, or is connectable with, an electro-stimulation unit.

Although the temperature control mechanism can include any suitable component that is capable of heating and/or cooling the probe head, in some implementations, the temperature control mechanism includes a thermoelectric device, such as a Peltier circuit that is able to heat and cool the probe head, or vice versa, as current passes through the chip. In other implementations, however, the temperature control mechanism comprises a mechanism that uses a thermally-conductive fluid to heat and/or cool the probe head.

While the temperature control mechanism can heat and/or cool the probe head to any suitable temperature, in some instances, the temperature control mechanism is able to heat the probe head to a temperature between about 104° and about 120° Fahrenheit ("F") (e.g., up to about 112° F.). Furthermore, in some instances, the temperature control mechanism is able to cool the probe head to a temperature that is below about 50° F. (e.g., about 25° to less than about 50° F.).

The electro-stimulation unit can comprise any device that is capable of providing electro-stimulation to a patient through the probe head. One example of such a device is a conventional TENS unit. Although in some embodiments, the probe device is connected to the electro-stimulation unit through the use of one or more electrical leads (e.g., wires and/or cables), in some implementations, the electro-stimulation unit is disposed in (or as part of) the probe device.

While the methods and process of the present invention can be particularly useful in the area of TENS treatments, those skilled in the art can appreciate that the methods and processes can be used in a variety of different applications and in a variety of other areas to provide thermo-stimulation and electro-stimulation.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE SEVERAL VIEWS OF THE DRAWINGS

The features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

The present invention relates generally to a thermo-electro-stimulation probe device that is capable of applying heating, cooling, and/or applying electrical current and/or stimulation to a patient as part of a thermo-electrotherapy treatment.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in another embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided (such as examples of suitable probe head shapes, materials, power supplies, TENS units, fluid exchangers, etc.) to provide a thorough understanding of embodiments of the invention. One having ordinary skill in the relevant art will recognize, however, that the invention may be practiced without one or more of the specific details, or with other methods, components, materials, and so forth. In other instances, well-known structures, devices, materials, or operations are not shown or described in detail to avoid obscuring aspects of the invention.

In addition, as the terms on, disposed on, attached to, connected to, coupled to, etc. are used herein, one object (e.g., a material, element, structure, member, etc.) can be on, disposed on, attached to, connected to, or coupled to another object—regardless of whether the one object is directly on, attached, connected, or coupled to the other object, or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

Figure 1:
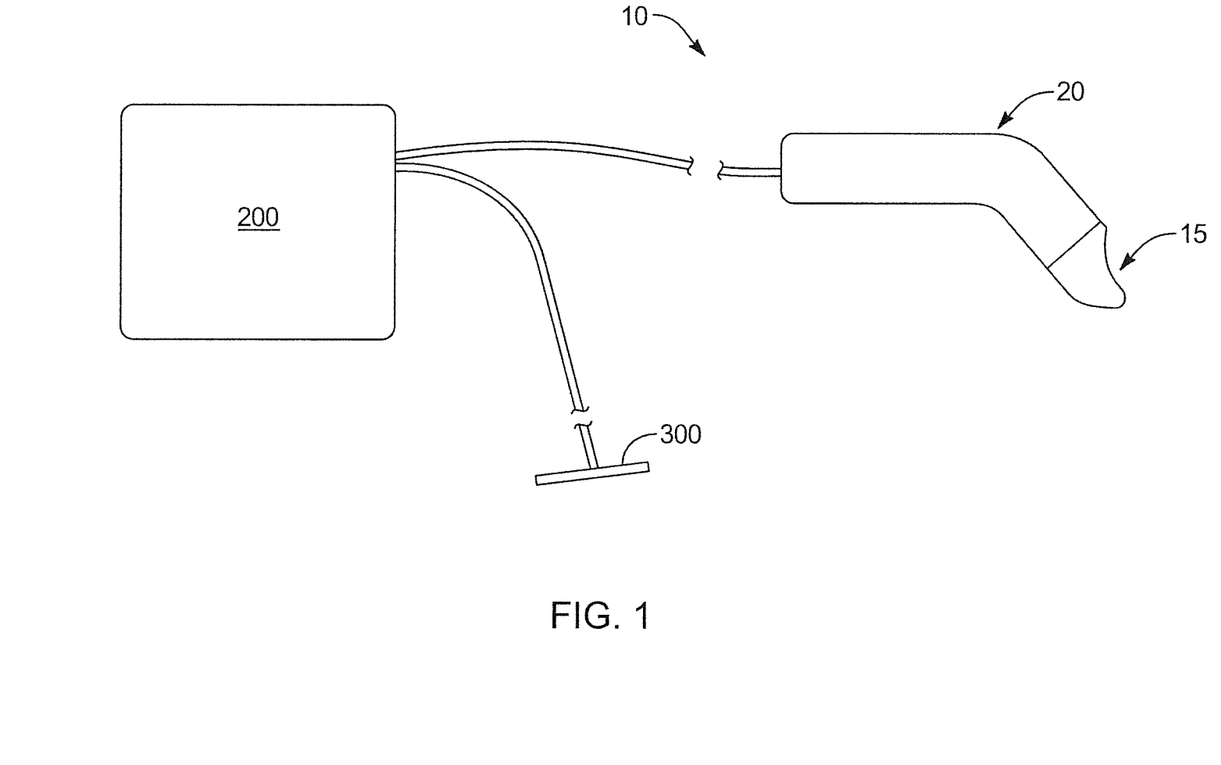
FIG. 1 illustrates a schematic view of a representative embodiment of a system comprising a thermo-electro-stimulation probe device.

According to some embodiments, the present invention provides a hand-held, thermo-electro-stimulation probe (probe or probe device) that is capable of heating and cooling, as well as applying electro-stimulation to, a patient as part of an thermo-electrotherapy treatment. While the probe can comprise any suitable component that allows it to perform such functions, FIG. 1 shows a representative embodiment in which the hand-held, thermo-electro-stimulation probe device 10 comprises a probe head 15 and a probe body 20 that is configured to attach as an accessory to an electro-stimulation unit 200, which can comprise one or more return leads 300. To provide a better understanding of the described probe, a more detailed description of the probe, and its various components, is provided below.

With respect to the probe head 15, the probe head can have any suitable component or characteristic that allows it to be used to apply pressure and motion, to heat and/or cool, and to apply electro-stimulation (e.g., current, electrical impulses, etc.) to a localized area of a patient. For instance, the probe head can comprise any suitable material that is both thermally-conductive and electrically-conductive. Some non-limiting embodiments of suitable materials used in the probe head include one or more metallic materials, such as aluminum, copper, stainless steel (or other iron based alloys), and/or gold; electro-ceramics, such as indium tin oxide, ianthanum-doped strontium titanate, yttrium-doped strontium titanate, etc., in a biocompatible configuration; and/or any other suitable electrically and thermally-conductive materials. Indeed, in some embodiments, the probe head comprises aluminum.

Figures 2A, 2B, 2D:
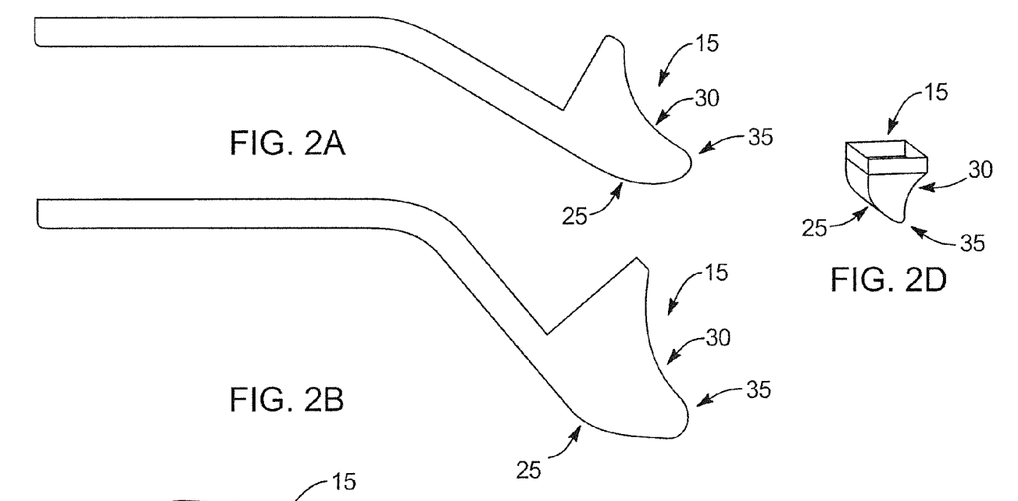
FIGS. 2A-2B each illustrate a side, plan view of a representative embodiment of a probe head.
FIGS. 2C-2E each illustrate a side, perspective view of a different representative embodiment of the probe head.
Figure 2C:
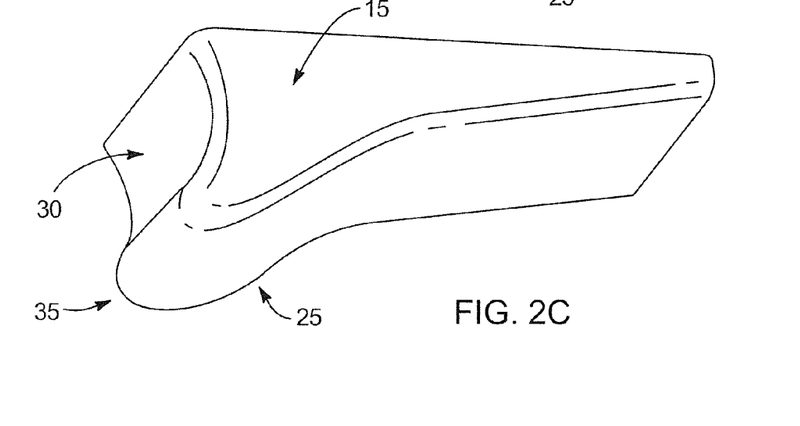

The probe head 15 can comprise any suitable shape, texture, and feature that allows it to assist in applying electro-stimulation, thermo-stimulation, and/or pressure to a patient. In one example, the probe head 15 comprises any suitable convex outer (or articulation) surface 25 (e.g., as shown in FIGS. 2A-2D) that allows the probe head 15 to provide direct pressure to a localized area of a patient. While such convex surface can be disposed in any suitable location that allows the probe 10 to function as intended, FIGS. 2A-2C show that, in some embodiments, the convex surface 25 is disposed on an underside of the probe head 15.

In another example of a suitable characteristic of the probe head 15, some embodiments of the probe head further comprises one or more concave articulation surfaces 30 (as shown in FIGS. 2A-2E). While such surfaces can be disposed in any suitable location, FIGS. 2A-2C show some embodiments in which the concave surface 30 is disposed on an upper surface of the probe head 15.

In still another example, FIGS. 2A-2E shows that some embodiments of the probe head 15 taper to a tip 35, which can (among other things) allow a relatively small portion of the probe head to contact a patient. Although this tip can be disposed in any suitable locations, FIGS. 2A-2D illustrate that, in at least some embodiments, the tip 35 (or peak) of the probe head 15 is at least partially disposed between the convex surface 25 and the concave surface 30.

Figure 2E:
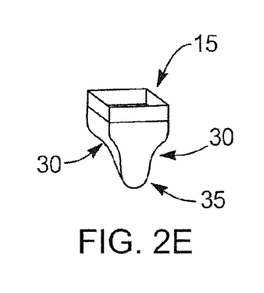
Figure 3:
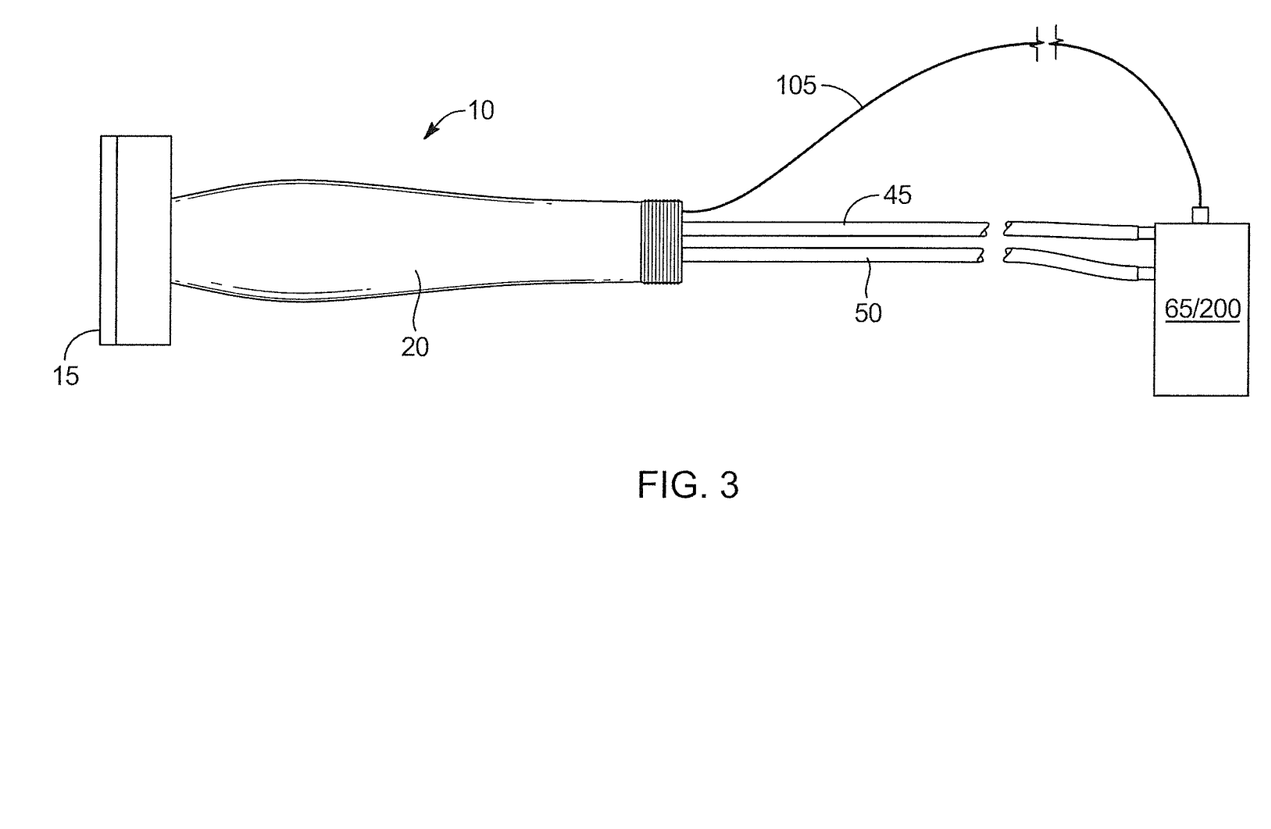
FIG. 3 illustrates a schematic view of a representative embodiment of the probe device.

In addition to the aforementioned characteristics, the probe head 15 can have any other suitable characteristic. Indeed, in one example, FIGS. 2D-2E show that some embodiments of the probe head 15 are substantially hollow. Although such a characteristic may provide the probe head with any suitable functionality, in some instances, it allows the probe head to be heated and/or cooled in a relatively short period of time. In another example, FIG. 3 shows that in some embodiments, the probe head 15 has a substantially flat profile. In still another example, however, FIG. 4 (and FIG. 6A) shows that some embodiments of the probe head 15 are substantially domed-shaped.

Figure 4:
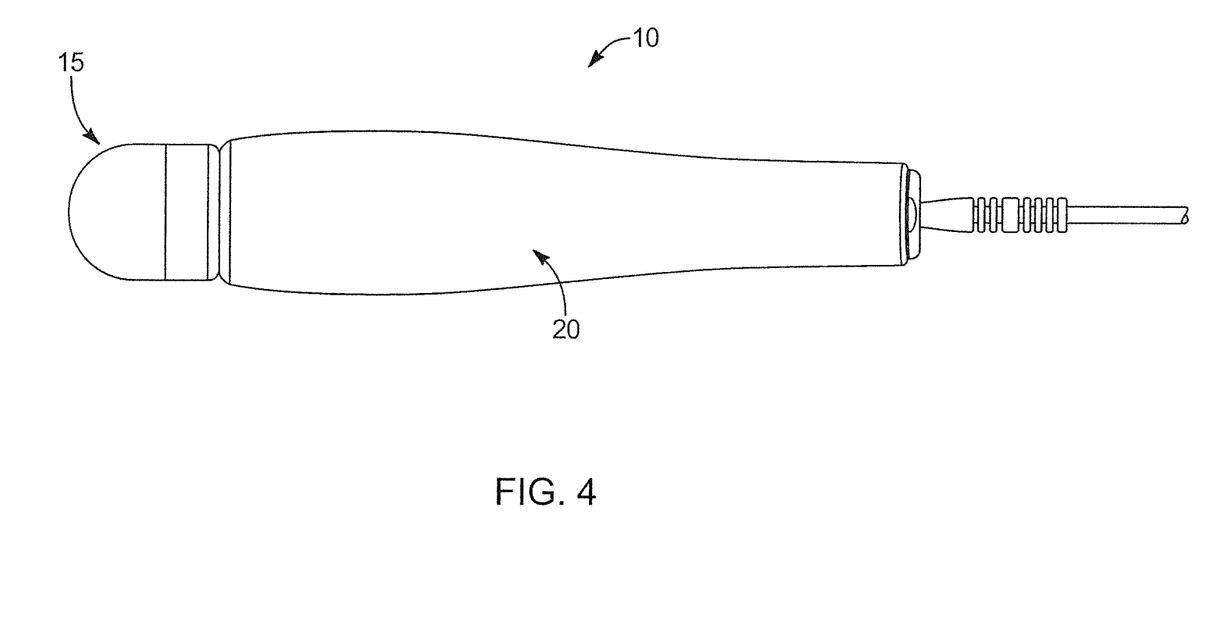
FIG. 4 illustrates a schematic view of another representative embodiment of the probe device.
Figure 5:
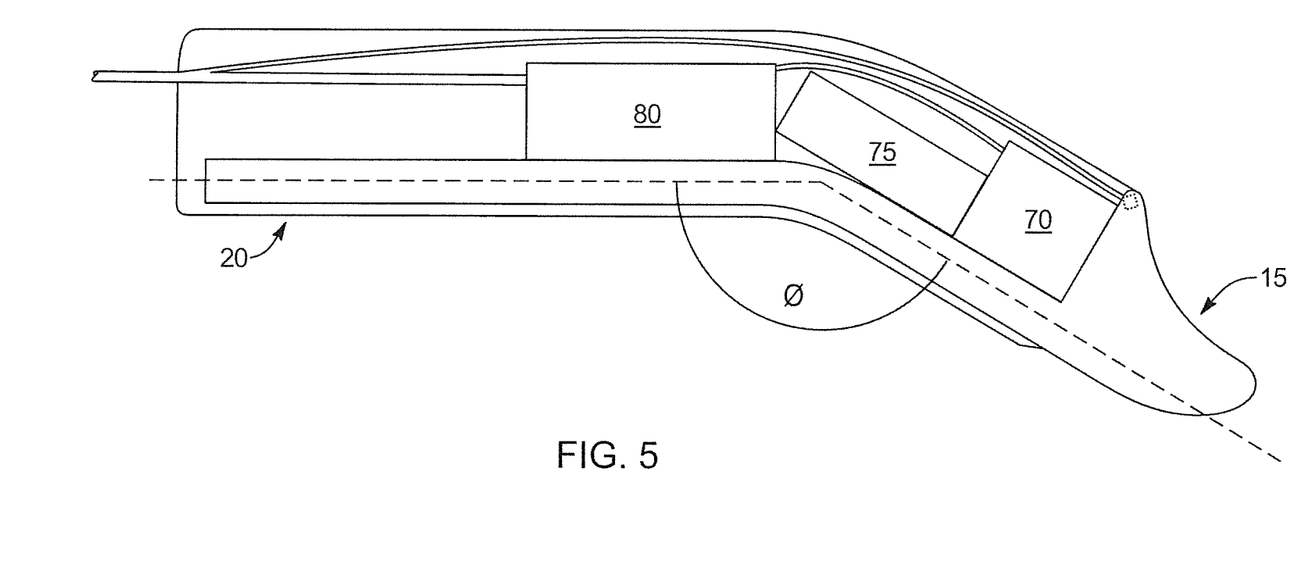
FIG. 5 illustrates a cross-sectional view of a representative embodiment of the probe device, wherein the probe device comprises a thermoelectric device.

With respect to the probe body 20, the body probe body can comprise any suitable characteristic that allows it to be held in, and moved around with, one or both of a user's hands. For instance, the probe body can contoured ergonomically, in any suitable manner. Additionally, although the probe body 20 can be any suitable shape, some embodiments of the probe body 20 (as shown in FIGS. 4 and 5) are generally elongated. Moreover, while FIG. 4 shows that some embodiments of the probe body 20 are substantially straight, FIG. 5 shows that some embodiments of the probe body 20 are bent (or comprise a bent portion). Where the probe body comprises a bent portion, the probe body can be bent at any suitable angle θ that is less that about 180°. Indeed, in some embodiments, the probe body is bent at any suitable angle between about 100° and about 170° (e.g., between about 125° and about 155°). While such a bend may perform any suitable function, in some embodiments, it allows a user to easily hold the probe device 10 in one hand, and to contact a patient with the probe head without contacting the patient with the user's hand that is holding the device.

The probe body 20 can comprise any suitable material that allows it to be held by a user. In some embodiments, the probe body comprises a non-electrically-conductive material, which permits a user to handle the probe body 20 without being exposed to an electrical current delivered to the probe head 15. In some embodiments, the material of probe body 20 is optionally selected to be somewhat thermally conductive while being electrically non-conductive. Thus, in such embodiments, the user may sense (to some extent) the temperature of the probe head 15 by holding the probe device 10. In some other embodiments, however, the material of the probe body 20 is optionally selected to substantially insulate the user from the changing temperature of the probe head. Some examples of suitable materials for the probe body include, but are not limited to, one or more polymers, plastics, ceramics, rubbers, and/or other non-electrically conductive materials.

The probe head 15 can be heated and cooled in any suitable manner that allows the probe device 10 to be used in a thermo-stimulation treatment (e.g., to heat and/or cool a portion of a patient). Indeed, the temperature of the probe head can be varied through the use of any suitable temperature control mechanism. In this regard, some examples of suitable temperature control mechanism include, but are not limited to, one or more fluid exchangers that circulate a thermally-conductive fluid, thermoelectric devices, heating elements, cooling elements, refrigeration units, fans, heat sinks, and/or any other suitable device that is capable of heating and/or cooling the probe head.

In some embodiments, the temperature control mechanism that controls the temperature of the probe head 15 comprises a fluid that is cycled through a portion of the probe device 10. In this regard, the fluid can comprise any suitable thermally-conductive fluid, including, without limitation, water, antifreeze (e.g., propylene glycol), oil, air, gas, and/or any other suitable material that is capable of flowing through the probe device and changing the temperature of the probe head sufficiently to allow the probe device to be used in a thermo-stimulation treatment.

Where the probe head 15 is heated through the use of a fluid, the probe device 10 can comprise any suitable component and characteristic that allows the fluid to heat and/or cool the probe head. Some non-limiting examples of such components include, without limitation, one or more internal fluid chambers in the probe device, conduits that bring the fluid into close proximity with the probe head, seals, and/or any other components that allow the fluid to raise and/or lower the probe head's temperature.

Figure 6A:
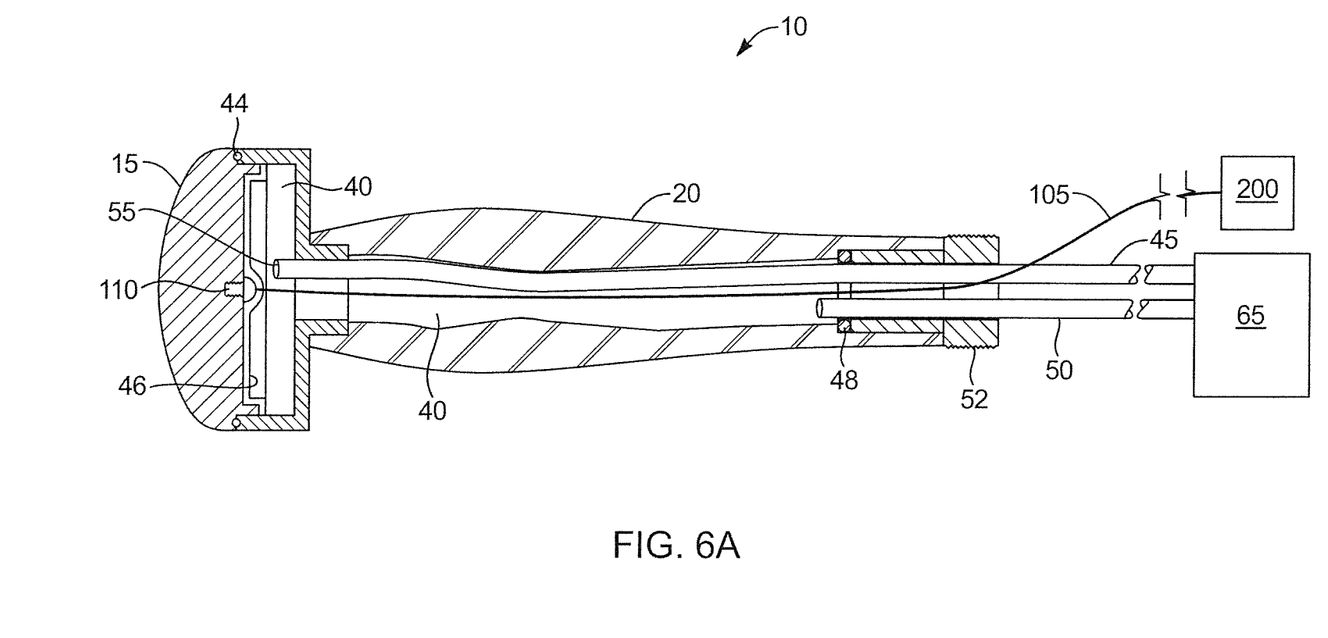
FIG. 6A illustrates a cross-sectional view of a representative embodiment of the probe device, wherein the probe device uses a fluid to regulate a temperature of the probe head.
Figure 6B:
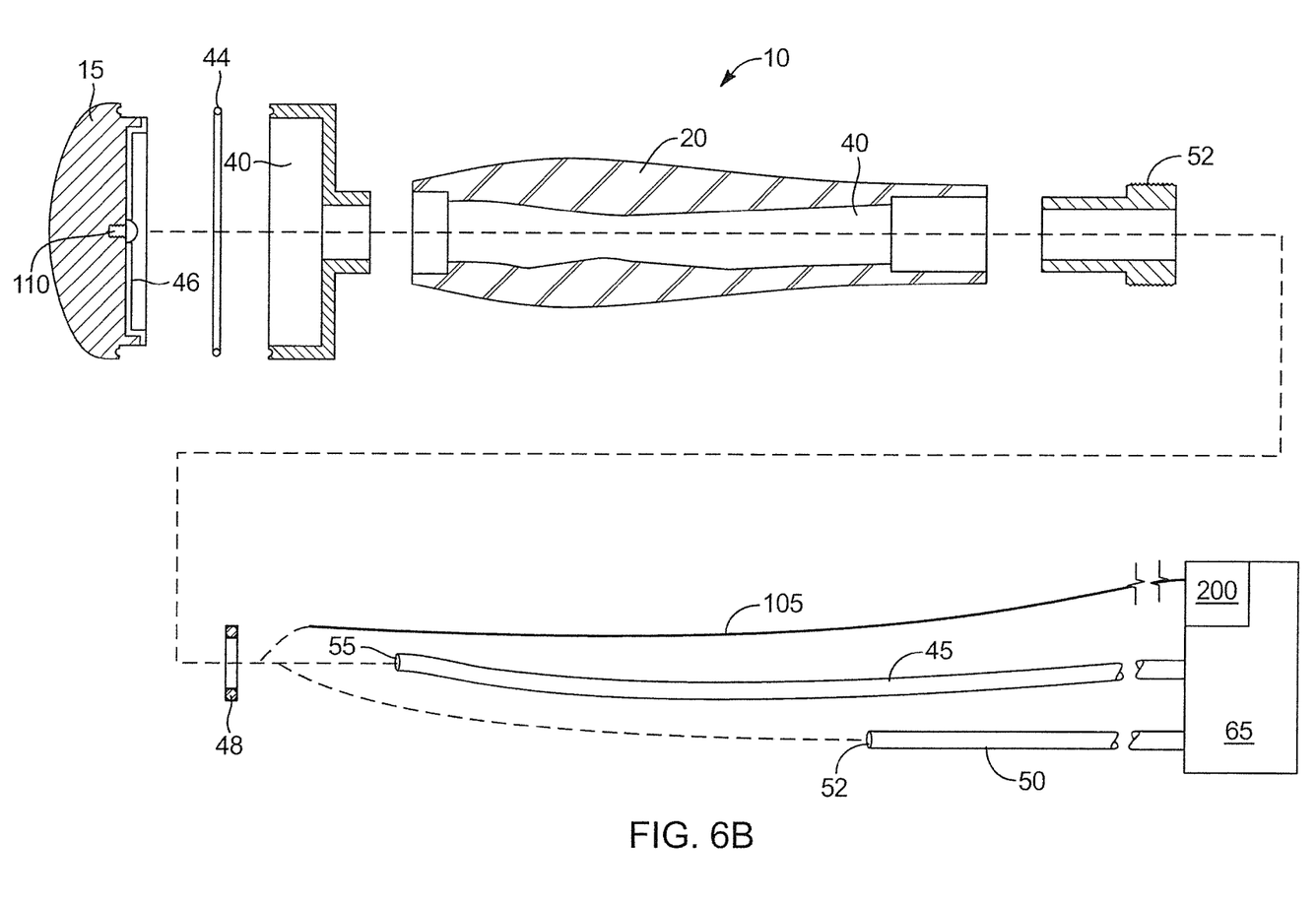
FIG. 6B illustrates a cross-sectional, exploded view of the probe device of FIG. 6A.

By way of non-limiting illustration, FIGS. 6A-6B show some embodiments in which the probe device 10 comprises an internal fluid chamber 40, an ingress line 45, and an egress line 50. Additionally, to ensure that the internal chamber 40 is fluid tight, FIGS. 6A-6B show that, in some embodiments, the probe device 10 comprises one or more gaskets 44, barriers 46, O-rings 48, adhesive bonds, and/or other seals 52. In accordance with some such embodiments, FIGS. 6A-6B show that while an opening 55 at a distal end 60 of the ingress line 45 is disposed distally in the probe device 10 (e.g., in proximity to the probe head 15), an opening 52 to the egress line 50 is disposed more proximally in the probe device 10. As such, fluid exiting from the ingress line is able to heat or cool the probe head and is then able to exit the probe device through the egress line, thereby, allowing the fluid to vary the temperature of the probe head with little thermal energy loss. Thus, fluid within the fluid chamber 40 is able to be drawn into, or cycled through, the fluid chamber 40 by the ingress line and/or the egress line. To further reduce thermal energy loss, in some embodiments, the ingress line and/or the egress line comprise an insulated conduit that is configured to help maintain a temperature of the fluid as it flows into and/or out of the probe device.

While the fluid can flow through the probe device 10 in any suitable manner, some embodiments of the present invention operate by maintaining a substantially constant flow of fluid from the fluid chamber 40 via the ingress line 45 and egress line 50. Accordingly, in such embodiments, the rate of fluid flow from the ingress line 45 is substantially equal to the rate of fluid flow into egress line 50, thereby establishing an equilibrium of fluid flow through the probe device 10.

Where the temperature of the probe head 15 is varied through the use of a fluid, the temperature of the fluid can be controlled in any suitable manner, including, without limitation, through the use of a fluid exchanger 65. In this regard, the fluid exchanger can comprise any suitable component that allows it to sufficiently heat and/or cool the fluid to provide the probe head with a desired temperature. In some embodiments, the fluid exchanger comprises one or more heating elements, cooling elements, thermoelectric devices, refrigeration units, fans, heat sinks, pumps, and/or any other suitable device that is capable of heating, cooling, and/or pumping the fluid.

Where the temperature control mechanism comprises a fluid exchanger 65, the fluid exchanger can be disposed in any suitable location that allows it to perform its intended function. Indeed, in accordance with some embodiments, FIG. 6A shows the fluid exchanger 64 is disposed externally from the probe device 10 and separate from the electro-stimulation unit 200. In other embodiments, however, the fluid exchanger can comprise part of the electro-stimulation device, or vice versa (as shown in FIG. 6B where the electro-stimulation unit 200 is part of the fluid exchanger 200). In still other embodiments (not shown), all or any suitable portion of the fluid exchanger is disposed within the probe device 10.

In some embodiments, the temperature control mechanism that controls the temperature of the probe head 15 comprises one or more thermoelectric devices. In such embodiments, the thermoelectric device can comprise any suitable component that is heated when current passes through the device in one direction and then cooled when current is passed through the device in the opposite direction. Some examples of such devices include, without limitation, Peltier circuits, Seebeck circuits, etc. In some embodiments, however, the thermoelectric device comprises a Peltier circuit.

Where the probe device 10 comprises a thermoelectric device (e.g., a Peltier circuit), the thermoelectric device can operate at any suitable voltage that allows the thermoelectric device to properly heat and/or cool the probe head 15. In some embodiments, the thermoelectric device operates between about 0 and about 20 volts (e.g., direct current). In other embodiments, the thermoelectric device operates at between about 2 and about 10 volts. In still other embodiments, the thermoelectric device operates at between about 3 and about 8 volts. In still other embodiments, the thermoelectric device operates in any suitable sub-range of the aforementioned ranges.

The thermoelectric device can also operate at any suitable current that allows the probe device 10 to function as intended. Indeed, in some embodiments, the thermoelectric device operates at a current between about 0 and about 20 amps. In other embodiments, the thermoelectric device operates at a current between about 5 and about 15 amps. In still other embodiments, the thermoelectric device operates in any suitable sub-range of the aforementioned ranges.

The thermoelectric device can also operate at any suitable power that allows the probe device 10 to function as intended. Indeed, in some embodiments, the thermoelectric device operates at a power between about 0 and about 200 watts. In other embodiments, the thermoelectric device operates at a current between about 5 and about 145 watts. In still other embodiments, the thermoelectric device operates in any suitable sub-range of the aforementioned ranges.

Where the probe device 10 comprises the thermoelectric device, the thermoelectric device can be disposed in any suitable location that allows it to properly change the temperature of the probe head 15. In one non-limiting illustration, FIG. 7 shows the thermoelectric device 70 is disposed so as to be in thermal communication with (e.g., to touch, to touch a thermally-conductive material that touches, and/or to be in close proximity with) the probe head 15.

Where the thermoelectric device 70 is used to vary the temperature of the probe head 15, the probe device 10 can comprise any other suitable component that allows the temperature of the probe head to be heated and cooled sufficiently to be useful in a thermo-stimulation procedure. In this regard, some examples such components include, but are not limited to, one or more heat sinks (e.g., any suitable heat sink, such as a pin fin, a straight fin, a cross-cut, a flared fin heat sink, etc.); a power source (e.g., any suitable electric power converter, transformer, battery, power supply, etc.); suitable dielectric (e.g., air, etc.); fan; and/or any other suitable component.

Figure 7:
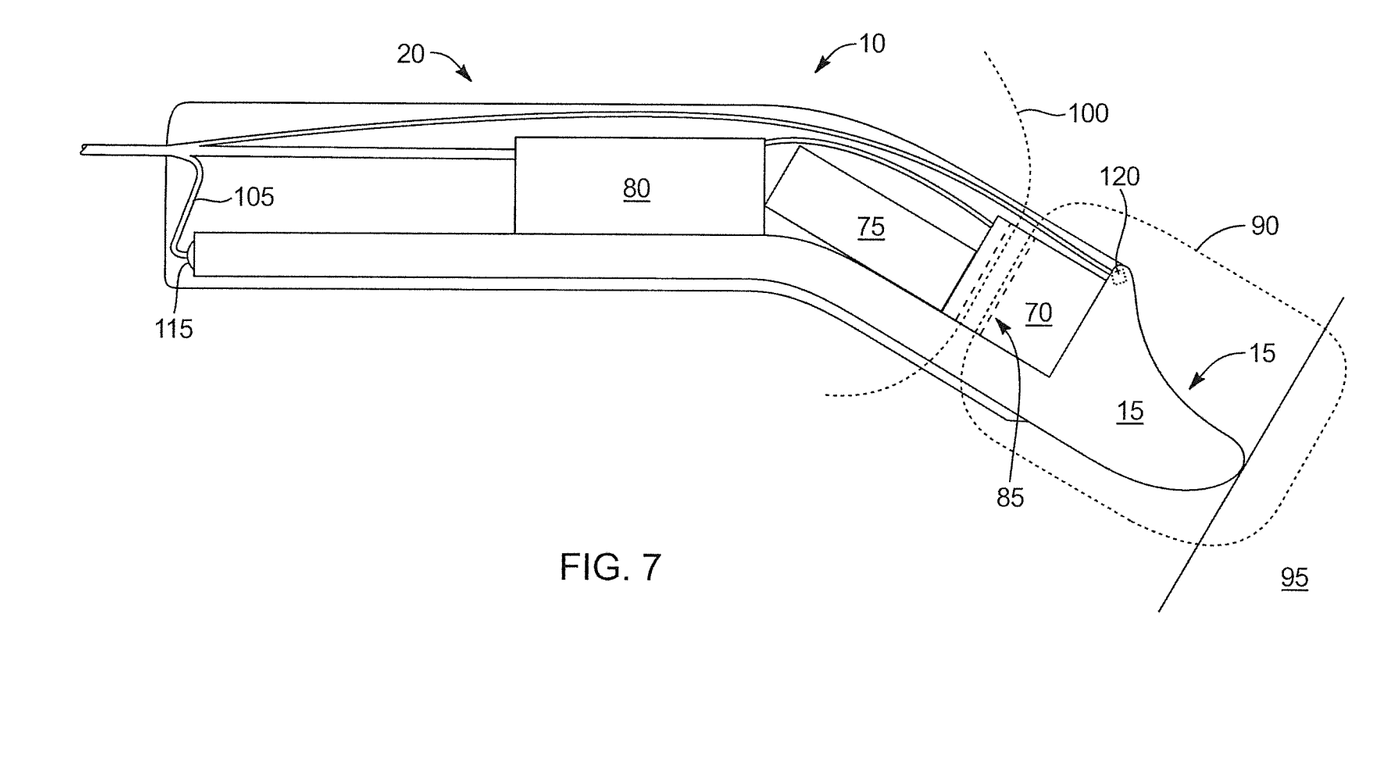
FIGS. 7-8 each illustrate a cross-sectional view of a different representative embodiment of the probe device, wherein the probe device in each Figure comprises the thermoelectric device to control the temperature of the probe head.

By way of non-limiting illustration, FIG. 7 illustrates an embodiment in which the probe device 10 comprises a heat sink 75 that is in thermal contact with the thermoelectric device 70 and a power source 80 that is in electrical contact with the thermoelectric device. Additionally, FIG. 7 further illustrates an embodiment in which the probe device 10 comprises a dielectric material 85 that passes through the thermoelectric device 70 to separate a patient connected circuit 90 (which runs through a patient 95) from a non-patient connected circuit 100 (e.g., in accordance with general standard IEC60601-1 published by the International Electrotechnical Commission).

The temperature control mechanism (e.g., the thermoelectric device 70, the fluid exchanger 65, etc.) can be configured to vary the temperature of the probe head 15 by any suitable amount that allows the probe head to be used in a thermo-stimulation treatment. Indeed, in some embodiments, the temperature control mechanism is configured such that the probe head is able to raise to any temperature between about 104 and about 120° F. In other embodiments, the temperature control mechanism is configured to heat the probe head to a temperature between about 105° and about 115° F. In still other embodiments, the temperature control mechanism is configured to heat the probe head to a temperature between about 106° and about 112° F. In still other embodiments, the temperature control mechanism is configured to heat the probe head up to any suitable sub-range of the aforementioned temperature ranges (e.g., about 112°±2° F.).

In some embodiments, the temperature control mechanism is configured to cool the probe head 15 to a temperature that is between about 50° and about 25° F. In other embodiments, the temperature control mechanism is configured to cool the probe head to a temperature between about 34° and about 49° F. In still other embodiments, the temperature control mechanism is configured to cool the probe head to a temperature between about 35° and about 40° F. In still other embodiments, the temperature control mechanism is configured to cool the probe head to any suitable sub-range of the aforementioned temperature ranges (e.g., about 36°±2° F.).

The temperature control mechanism (e.g., the thermoelectric device 70, the fluid exchanger 65, etc.) can be configured to vary the temperature of the probe head 15 by any suitable amount and at any suitable rate that allows the probe device 10 to be used in an effective thermo-therapy treatment. In some non-limiting embodiments, the temperature control mechanism is configured to vary the temperature of the probe head (e.g., from a coldest point to a hottest point in a cycle or vice versa) by between about 54° and about 100° Fahrenheit in any suitable amount of time. In this regard, some embodiments of the temperature control mechanism are configured to the vary the temperature of the probe head by between about 54° and about 95° F. in as little time as about 45 to about 60 seconds (or any sub-range thereof). In other embodiments, the temperature control mechanism is configured to vary the temperature of the probe head by between about 60° and about 90° in as little time as about 45 to about 60 seconds (or any sub-range thereof). In still other embodiments, the temperature control mechanism is able to vary the temperature of the probe head by between about 70° and about 80° in as little time as about 45 to about 60 seconds (or any sub-range thereof). Indeed, in some instances, the probe device 10 is configured to change the temperature of the probe head from about 35° to about 112° F. (e.g., about 77° F.) in as little time as about 45 to about 60 seconds. In yet other embodiments, the temperature control mechanism is able to vary the probe head's temperature by any suitable sub-range of the temperatures provided above, in as little as about 45 to about 60 seconds (or any sub-range thereof). While varying the temperature at the above-mentioned rates may provide the probe device with several beneficial characteristics, in some embodiments, the temperature control mechanism varies the temperature of the probe head at a rate that protects the thermoelectric device 70 from shock that can come with varying the temperature too quickly.

As discussed previously, some embodiments of the probe device 10 are configured to provide electro-stimulation to a patient through the probe head 15. In such embodiments, the electro-stimulation can be provided to the probe head in any suitable manner. Indeed, in some embodiments, the probe device 10 is attached to (or selectively attachable to and detachable from) an electro-stimulation unit 200. In this regard, the electro-stimulation unit can comprise any known or novel electro-stimulation device that is capable of providing electro-stimulation to a patient via the probe head. Some examples of suitable electro-stimulation devices comprise any suitable TENS unit (e.g., the Dynatron Solaris® Plus series, Dynatron Solaris® series, Dynatron® 50 Plus series, and Dynatron® 25 series, produced by Dynatronics, Corp. in Salt Lake City, Utah); electro muscle stimulation unit; cranial electrical stimulation unit; TES unit; etc. In some embodiments, however, the probe device 10 attaches to a TENS unit.

The probe head 15 can be electrically coupled to the electro-stimulation unit 200 in any suitable manner. Indeed, in some embodiments, the probe head is electrically connected or connectable to the electro-stimulation unit through the use of one or more leads 105 (e.g., wires and/or cables). In such embodiments, the leads can connect to the probe head in any suitable manner, including, without limitation, through one or more fasteners (e.g., crimps, set screws 110 as shown in FIG. 6B), solder joints 115 (as shown in FIG. 7), welds, electrically-conductive epoxies, electrical connectors, and/or any other suitable method that is capable of electrically coupling the probe head to the lead.

In some embodiments (e.g., embodiments in which the probe device 10 uses fluid to control the temperature of the probe head 15), the probe head and electrical connections between the probe head and the electro-stimulation unit 200 are electronically insulated (e.g., from the fluid). In such embodiments, the probe head and its corresponding electrical connections can be electrically isolated (e.g., from the fluid) in any suitable manner, including, without limitation, through the use of external sheathing on any leads; a housing which provides a fluid tight barrier between the probe head, the leads, and any fluid within the internal chamber; an electronically-insulating barrier 46 that prevents contact between a fluid in the internal chamber 40 and the probe head 15; and/or any other suitable component that is capable of insulating the electrical circuit running between the probe head and the electro-stimulation unit.

The probe device 10 can be electrically connected to the electro-stimulation device 200 in any suitable manner. Indeed, in some embodiments, the probe device is integrally connected to the electro-stimulation unit (e.g., is hard-wired to the electro-stimulation unit). In other embodiments, however, the probe device is selectively attachable to and detachable from the electro-stimulation unit. In such embodiments, the probe device can connect to the electro-stimulation unit in any suitable manner, including, without limitation, through the use of one or more a banana jacks, USB connectors, stereo jacks, and/or any other suitable electrical connectors. Accordingly, in some such embodiments, the probe device can be used as an accessory that can be added to virtually any suitable electro-stimulation unit.

Figure 8:
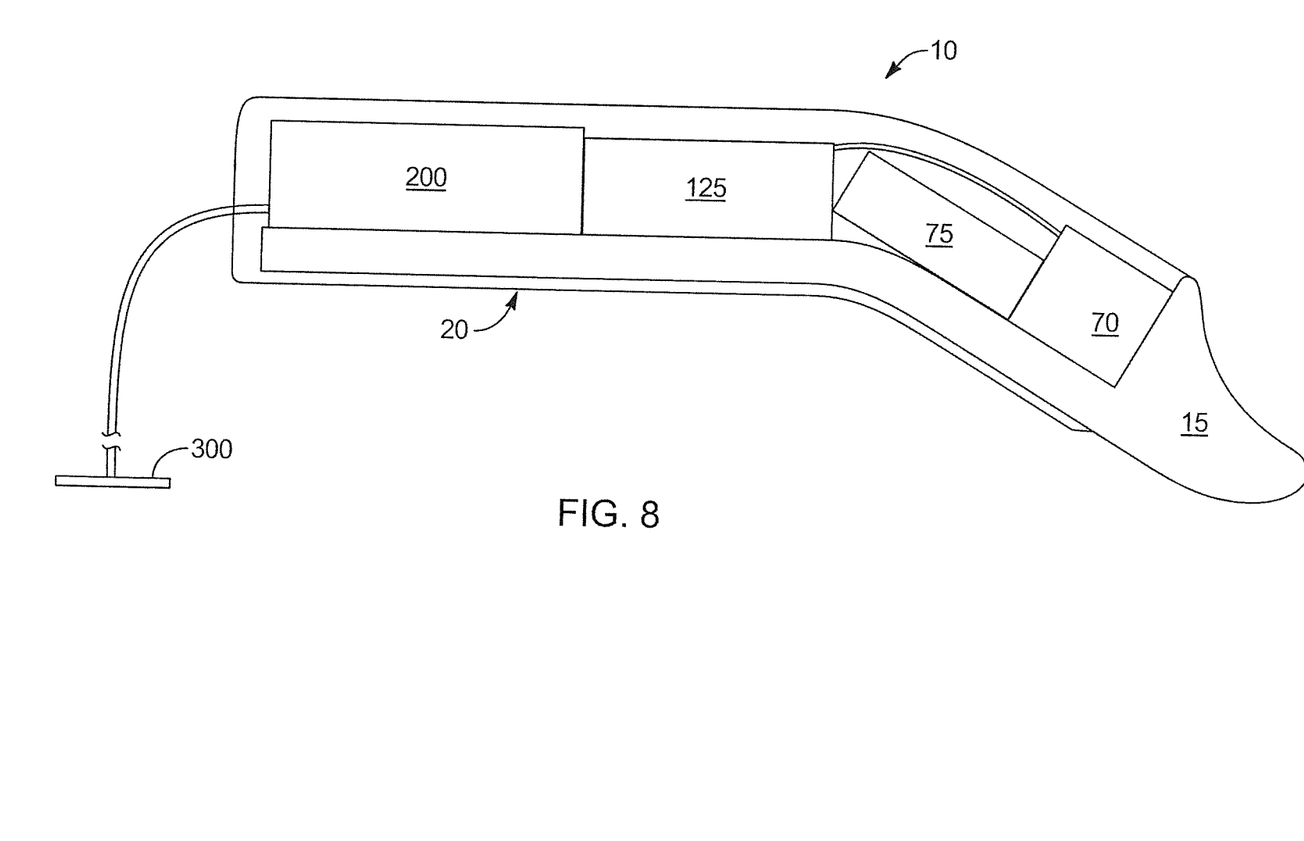

The electro-stimulation unit 200 can be disposed in any suitable relation with respect to the probe device 10 that allows the probe device to function as intended. Indeed, as previously discussed, the electro-stimulation unit can be disposed outside of the probe device (e.g., as a separate unit, as part of the fluid exchanger 65, etc.). In some other embodiments, however, the electro-stimulation unit is disposed on or in the probe device. In such embodiments, the electro-stimulation unit can be integrated into the probe device in any suitable manner. By way of non-limiting illustration, FIG. 8 shows that, in some embodiments, the electro-stimulation unit 200 is disposed within the probe body 20. In such embodiments, the probe device can comprise any other suitable component that allows it to function as intended. By way of example, FIG. 8 shows that, in some embodiments, a return electrode 300 is able to electrically connect to the probe device 10 in order properly isolate a patient.

The described systems and methods can be used in or with any suitable operating environment and/or software. In this regard, FIG. 9 and the corresponding discussion are intended to provide a general description of a suitable operating environment (e.g., of the electro-stimulation unit 200, the fluid exchanger 65, and/or other operating environment that controls or otherwise interacts with the probe device) in accordance with some embodiments of the described systems and methods. As will be further discussed below, some embodiments embrace the use of one or more processing (including, without limitation, micro-processing) units in a variety of customizable enterprise configurations.

Some embodiments of the described systems and methods embrace one or more computer readable media, wherein each medium may be configured to include or includes thereon data or computer executable instructions for manipulating data. The computer executable instructions include data structures, objects, programs, routines, or other program modules that may be accessed by one or more processors, such as one associated with a general-purpose processing unit capable of performing various different functions or one associated with a special-purpose processing unit capable of performing a limited number of functions.

Computer executable instructions cause the one or more processors of the enterprise to perform a particular function or group of functions and are examples of program code means for implementing steps for methods of processing. Furthermore, a particular sequence of the executable instructions provides an example of corresponding acts that may be used to implement such steps.

Examples of computer readable media (including non-transitory computer readable media) include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing unit.

Figure 9:
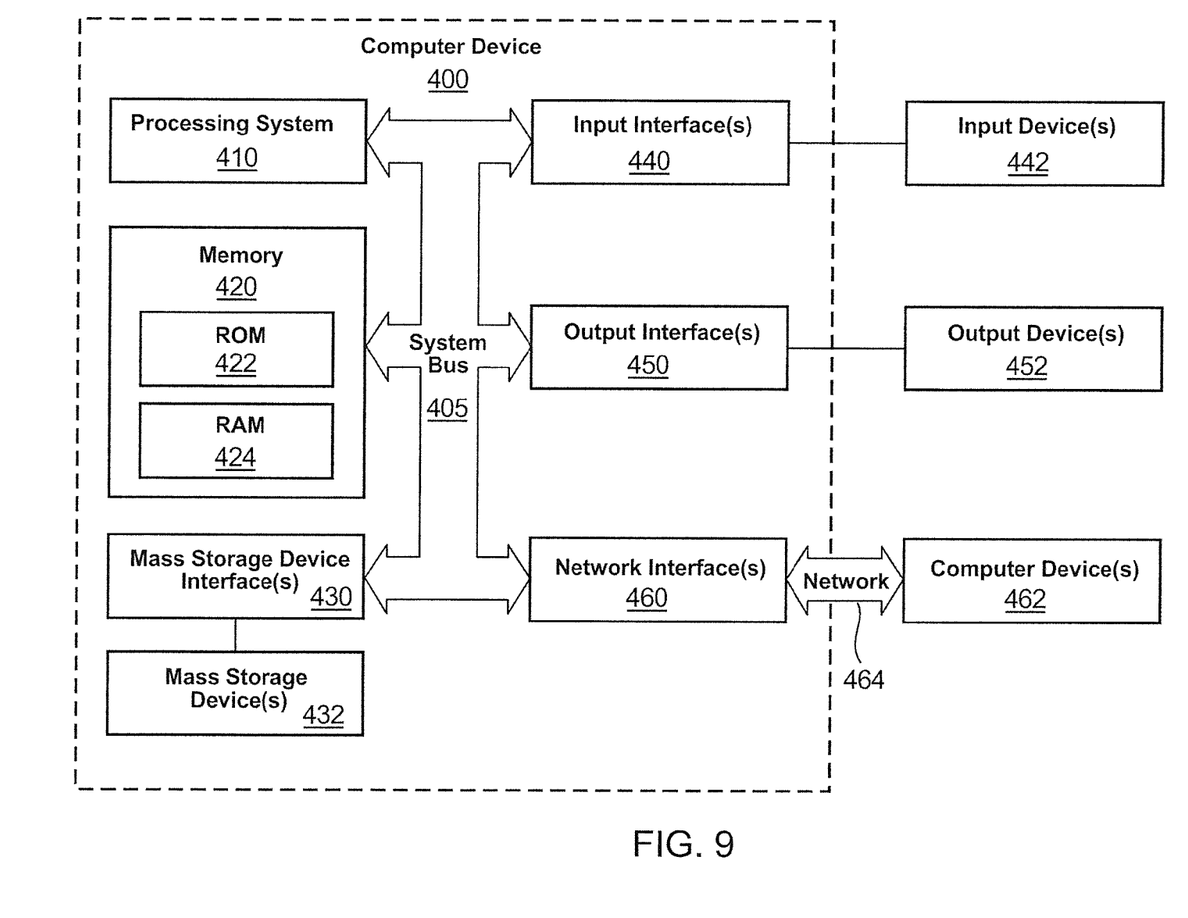
FIG. 9 illustrates a representative system that provides a suitable operating environment for use in some embodiments of the present invention.

With reference to FIG. 9, a representative system includes computer device 400, which may be a general-purpose or special-purpose computer. For example, computer device 400 may be a personal computer, a notebook computer, a tablet computer, a processor system, a hand-held device, a workstation, a minicomputer, a mainframe, a supercomputer, a multi-processor system, a network computer, a processor-based consumer electronic device, or the like.

Computer device 400 includes system bus 405, which may be configured to connect various components thereof and enables data to be exchanged between two or more components. System bus 405 may include one of a variety of bus structures including a memory bus or memory controller, a peripheral bus, or a local bus that uses any of a variety of bus architectures. Typical components connected by system bus 405 include processing system 410 and memory 420. Other components may include one or more mass storage device interfaces 430, input interfaces 440, output interfaces 450, and/or network interfaces 460, each of which will be discussed below.

Processing system 410 includes one or more processors, such as a central processor and optionally one or more other processors designed to perform a particular function or task. It is typically processing system 410 that executes the instructions provided on computer readable media, such as on memory 420, a magnetic hard disk, a removable magnetic disk, a magnetic cassette, an optical disk, or from a communication connection, which may also be viewed as a computer readable medium.

Memory 420 includes one or more computer readable media that may be configured to include or includes thereon data or instructions for manipulating data, and may be accessed by processing system 420 through system bus 405. Memory 420 may include, for example, ROM 422, used to permanently store information, and/or RAM 424, used to temporarily store information. ROM 422 may include a basic input/output system ("BIOS") having one or more routines that are used to establish communication, such as during start-up of computer device 400. RAM 424 may include one or more program modules, such as one or more operating systems, application programs, and/or program data.

One or more mass storage device interfaces 430 may be used to connect one or more mass storage devices 432 to system bus 405. The mass storage devices 432 may be incorporated into or may be peripheral to computer device 400 and allow computer device 400 to retain large amounts of data. Optionally, one or more of the mass storage devices 432 may be removable from computer device 400. Examples of mass storage devices include hard disk drives, magnetic disk drives, tape drives, solid state mass storage, and optical disk drives. Examples of solid state mass storage include flash cards and memory sticks. A mass storage device 432 may read from and/or write to a magnetic hard disk, a removable magnetic disk, a magnetic cassette, an optical disk, or another computer readable medium. Mass storage devices 432 and their corresponding computer readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 440 may be employed to enable a user to enter data and/or instructions to computer device 400 through one or more corresponding input devices 442. Examples of such input devices include a keyboard and alternate input devices, such as a mouse, trackball, light pen, stylus, or other pointing device, a microphone, a joystick, a game pad, a satellite dish, a scanner, a camera, a touch screen, or another input device. Similarly, examples of input interfaces 440 that may be used to connect the input devices 442 to the system bus 405 include a serial port, a parallel port, a game port, a universal serial bus ("USB"), a firewire (IEEE 1394), or another interface.

One or more output interfaces 450 may be employed to connect one or more corresponding output devices 452 to system bus 405. Examples of output devices include a monitor or display screen, a speaker, a printer, and the like. A particular output device 452 may be integrated with or peripheral to computer device 400. Examples of output interfaces include a video adapter, an audio adapter, a parallel port, and the like.

One or more network interfaces 460 enable computer device 462 to exchange information with one or more other local or remote computer devices, illustrated as computer devices 462, via a network 464 that may include hardwired and/or wireless links. Examples of network interfaces include a network adapter for connection to a local area network ("LAN") or a modem, wireless link, or other adapter for connection to a wide area network ("WAN"), such as the Internet. The network interface 460 may be incorporated with or peripheral to computer device 400. In a networked system, accessible program modules or portions thereof may be stored in a remote memory storage device. Furthermore, in a networked system computer device 400 may participate in a distributed computing environment, where functions or tasks are performed by a plurality of networked computer devices. While those skilled in the art will appreciate that the invention may be practiced in networked computing environments with many types of computer system configurations.

In addition to, or in place of, the components discussed above with respect to FIG. 9, the operating environment of the described probe device 10 (i.e., the electro-stimulation unit 200, the fluid exchanger 65, and/or other operating environment that controls or otherwise interacts with the probe device) can comprise any other suitable component. In this regard, some examples of such components include, but are not limited to, one or more electrical signal generators, electrical signal amplifiers, modulation controllers, signal conditioners, frequency dividers, and/or any other component that may be used to provide electro-stimulation and/or thermo-stimulation through the probe head 15.

The described probe device 10 can be modified in any suitable manner that allows it to provide thereto-stimulation and/or electro-stimulation to a patient. In one example, the probe device comprises one or more temperature sensors (e.g., sensor 120 in FIG. 7) that are configured to determine the temperature of the thermoelectric device 70 and/or the probe head 15. In such embodiments, the temperature sensor can provide feedback (e.g., to the electro-stimulation unit, the fluid exchanger 65, and/or the probe itself) that indicates whether the probe head should be heated or cooled to reach and/or maintain a desired temperature. Thus, in some embodiments, the probe device comprises a closed-loop temperature control mechanism in which temperature of the probe head is able to be controlled relatively well.

In another example, while some embodiments of the probe device 10 are configured to obtain any needed power (e.g., to operate the thermoelectric device 70) from the electro-stimulation device 200. In some embodiments (such as those in which the electro-stimulation unit is disposed in the probe device), the probe device is configured to plug into a conventional socket-outlet (e.g., a socket that is connected to mains electricity).

In still other embodiments, the probe device is configured to include its own power source, such as one or more primary and/or secondary batteries. By way of non-limiting illustration, FIG. 8 shows an embodiment in which the probe device 10 comprises at least one battery 125. Where the probe device comprises its own power source (e.g., battery), such power source can be used for any suitable purpose. Indeed, in some embodiments in which the probe device comprises a temperature control mechanism (e.g., a Peltier circuit), the internal power source is configured to operate the temperature control mechanism. In other embodiments in which the probe device comprises an electro-stimulation unit (e.g., a TENS unit), the internal power source is configured to operate the electro-stimulation unit. In still other embodiments, the probe device's internal power source is configured to power the temperature control mechanism, the electro-stimulation unit, and/or any other suitable component of the probe device. Accordingly, some embodiments of the described invention can be used with relatively little equipment outside of the probe device.

In another example of how the probe device 10 can be modified, in some embodiments, the probe device optionally includes one or more vibration units (e.g., unbalanced spinning masses, oscillating masses, etc.) that are capable of vibrating the probe device. Accordingly, such embodiments may further increase the massaging capabilities of the probe device.

In still another example, the probe device 10 is optionally modified to include one or more light sources that are configured to provide any suitable wavelength (e.g., red light, blue light, infrared light, etc.) and intensity of light that is capable of being used to provide light therapy to a patient. In such embodiments, the light source can be disposed in any suitable location, including, without limitation, by being disposed around a perimeter of the probe head, being embedded within or otherwise disposed at the probe head, and/or being disposed in the probe body (e.g., near the probe head 15).

The described probe device 10 can be used in any suitable manner that allows it to heat, cool, and provide electro-stimulation to a portion of a patient's body. In some embodiments, however, an electrically-conductive gel (e.g., Ultrasound jell, ecoLotion™ for ultrasound applications, DynaMist™, etc.) is optionally placed between the patient and the probe head 15 to increase the effectiveness of the probe's electro-stimulation treatment. Additionally, in some embodiments, the probe device is manually moved across tissue of a patient's body to provide a desired treatment. Moreover, in some embodiments, the probe device is leaned to different degrees to vary the portion of the probe head that contacts a patient. In any case, the probe device can be used to treat any mild, acute, or chronic ailment that can benefit from the thermo-stimulation and/or electro-stimulation.

When the probe device 10 is used, the probe device can heat, cool, and/or provide electro-stimulation to a patient in any suitable manner. Indeed, the temperature of the probe head can be varied in any suitable manner that allows the probe device to be used for a desired thermo-electrotherapy treatment. Similarly, the probe device can be used to provide any suitable form of electro-stimulation that may be useful in an electro-stimulation treatment. In this regard, some examples of suitable types of electro-stimulation that can be provided through the probe device include, but are not limited to, interferential current therapy ("IFC"), premod, biphasic, medium frequency (Russian), high volt, micro-current, direct current stimulation, fixed frequency IFC/premod, etc. Additionally, while the probe device can be used to heat and/or cool without providing electro-stimulation during the heating/cooling process, in some embodiments, the probe device heats and/or cools the tissue as the probe device provides electro-stimulation. In this regard, the probe device is configurable to heat, cool, and/or provide electro-stimulation to a patient in any suitable combination.

In some embodiments, the probe device 10, the electro-stimulator device 200, the fluid exchanger 65, and/or any other component that is capable of controlling the probe device comprises software that enables a user to program, modify, and/or use a preprogrammed program that controls the temperature of the probe head, the time the probe head remains at desired temperatures, the transition time between desired temperatures, the electro-stimulation provided through the probe head, and/or any other programmable characteristic of the probe device. Accordingly, the probe device can be used to provide a wide variety of different thermo-stimulation and electro-stimulation treatments.

As discussed above, the described probe device 10 can have many beneficial characteristics. Indeed, in some embodiments, the probe device is capable using a single probe head to heat, cool, and provide electro-stimulation to a portion of a patient's body. As a result, such embodiments can provide an effective means for providing thermo-therapy and electro-therapy simultaneously. Accordingly, a patient and user of such embodiments may be able to save time by having both treatments be performed at overlapping time periods. Additionally, in embodiments in which thermo-stimulation and electro-stimulation are provided to a patient simultaneously, the two treatments may have synergistic effects that improve the efficiencies of the treatments. For example, while the application of electro-stimulation and/or a cold probe head 15 to a patient may reduce pain in the patient, a cold treatment may also reduce swelling and/or bleeding that can occur during an intense massage (e.g., a massage to break up scar tissue).

In another example of a beneficial characteristic, some embodiments of the described probe device 10 are hand-held, and as such, can be easily moved across a surface of a patient. As a result, some such embodiments can easily be used in any suitable massage treatment (or a treatment in which the probe device is manually moved across a tissue of a patient) and can even be used to treat relatively deep tissues. For instance, some embodiments of the probe device allow a user to dig the probe tip 35 into piece of tissue and to move the probe device in a desired manner (e.g., to break up scar tissue).

In still another example, some embodiments of the probe device are easily attachable to (and controllable by) a conventional electro-stimulation unit 200. Accordingly, such embodiments can easily increase the effectiveness and utility of such electro-stimulation units.

Thus, embodiments of the present invention relate generally to a thermo-electro-stimulation probe device that is capable of applying heating, cooling, and/or applying electrical current and/or stimulation to a patient as part of a thermo-electrotherapy treatment.

The present invention may be embodied in other specific forms without departing from its spirit or essential characteristics. The described embodiments and examples are all to be considered, in all respects, only as illustrative and not as being restrictive in any manner. The scope of the invention is, therefore, indicated by the appended claims, rather than by the foregoing description. All changes which come within the meaning and range of equivalency of the claims are to be embraced within their scope.

We claim:

1. A hand-held thermo-electro-stimulation probe device, comprising:
   a probe head that is configured to selectively articulate against an individual's skin and comprises an electrically and thermally-conductive material, wherein the probe head comprises:
      a unitary tip having a plurality of external surfaces, wherein at least one of the plurality of external surfaces comprises
      a convex curvature configuration, wherein the plurality of external surfaces form a plurality of external edges, and wherein the plurality of external edges and the plurality of external surfaces comprise the electrically and thermally-conductive material; and
   a temperature control mechanism comprising a thermoelectric device configured to raise and lower a temperature of the tip configured to cause the plurality of external surfaces and the plurality of external edges to selectively be warm and to selectively be cold to respectively heat and cool the individual's skin,
   wherein the probe head is attached to an electro-stimulation unit such that the probe head is configured to provide the individual with electro-stimulation simultaneously with thermo-stimulation.

2. The probe device of claim 1, wherein the thermo-electro-stimulation probe device further comprises a dielectric material that passes through the thermoelectric device in a manner that is configured to separate a patient connected circuit from a non-patient connected circuit.

3. The probe device of claim 1, wherein the hand-held probe comprises a handle, and wherein the handle comprises a bent portion having an angle between about 125 degrees and about 155 degrees.

4. The probe device of claim 1, wherein the temperature control mechanism is configured to use a fluid to raise and lower the temperature of the probe head.

5. The probe device of claim 1, wherein the electro-stimulation unit is disposed in the probe device.

6. The probe device of claim 1, wherein the hand-held probe comprises a self-contained power source.

7. The probe device of claim 1, wherein the hand-held probe comprises an accessory that is selectively attachable to and detachable from the electro-stimulation unit.

8. The probe device of claim 1, wherein the temperature control mechanism is able to raise the temperature of the probe head up to between about 105° Fahrenheit and about 120° Fahrenheit.

9. The probe device of claim 1, wherein the temperature control mechanism is able to lower the temperature of the probe head to below about 50° Fahrenheit.

10. The probe device of claim 1, wherein the temperature control device is capable of varying the temperature of the probe head by between about 54° and about 95° F. in as little as about 45 to about 60 seconds.

11. A hand-held thermo-electro-stimulation probe device, comprising:
   a probe head that is configured to selectively articulate against an individual's skin and comprises an electrically and thermally-conductive material, the probe head comprising:
      a tip having a plurality of external surfaces, wherein at least one of the plurality of external surfaces comprises a convex curvature configuration, wherein the plurality of external surfaces form a plurality of external edges, and wherein the plurality of external edges and the plurality of external surfaces comprise the electrically and thermally-conductive material; and
   a thermoelectric device configured to raise and lower a temperature of the tip configured to cause the plurality of external surfaces and the plurality of external edges to selectively be warm and to selectively be cold to respectively heat and cool the individual's skin,
   wherein the probe head is configured to attach to a transcutaneous electrical nerve stimulation unit such that the tip is configured to provide the individual's skin with both electro-stimulation and thermo-stimulation, and
   wherein a handle portion of the thermo-electrostimulation probe device is configured to insulate it's user from fluctuations in the temperature of the probe head.

12. The probe device of claim 11, wherein the thermoelectric device is programmable to vary the temperature of the tip in accordance with a set program.

13. The probe device of claim 12, wherein the program is configured to control a time that the tip remains at a desired temperature and a transition time between at least two temperatures.

14. The probe device of claim 11, wherein the hand-held probe comprises the transcutaneous electrical nerve stimulation unit.

15. The probe device of claim 11, wherein the probe device further comprises a temperature sensor configured to measure the temperature of the tip.

16. A method for using a probe device, the method comprising:
   obtaining an electro-stimulation probe device, comprising:
      a probe head that is configured to selectively articulate against an individual's skin and includes an electrically and thermally conductive and rigid material, wherein the probe head comprises:
         a tip having a plurality of external surfaces, wherein at least one of the plurality of external surfaces comprises a convex curvature configuration, wherein the plurality of external surfaces form a plurality of external edges, and wherein the plurality of external edges and the plurality of external surfaces comprise the electrically and thermally-conductive material; and
      wherein the probe device further comprises a temperature control mechanism comprising a thermoelectric device configured to raise and lower a temperature of the tip to cause the plurality of external surfaces and the plurality of external edges to selectively be warm and to selectively be cold to respectively heat and cool the individual's skin, wherein the probe head is electrically attached to the transcutaneous electrical nerve stimulation unit; and
   manually moving the hand-held probe across the individual's skin such that the tip provides the skin with electro-stimulation and thermo-stimulation.

17. The method of claim 16, further comprising using the probe device to break up scar tissue.

18. The method of claim 16, wherein the thermo-stimulation comprises lowering the temperature of the tip to below about 50° Fahrenheit.

19. The method of claim 16, wherein the thermo-stimulation comprises raising the temperature of the tip to between about 104° and about 120° Fahrenheit.

20. The method of claim 16, wherein the thermo-stimulation comprises varying the temperature of the tip by between about 54° and about 95° F. in as little as about 45 to about 60 seconds.

21. The method of claim 16, wherein the electro-stimulation probe device comprises:
   a dielectric material that passes through the thermoelectric device in a manner that is configured to separate a patient connected circuit from a non-patient connected circuit; and
   a return lead that is configured to be placed in contact with the individual's skin to close the patient connected circuit.

22. A thermo-electro-stimulation probe comprising:
   a probe head comprising a rigid material that is electrically and thermally conductive,
   wherein the probe head comprises:
      a tip having a plurality of external surfaces, wherein at least one of the plurality of external surfaces comprises a convex curvature configuration, wherein the plurality of external surfaces form a plurality of external edges, and wherein the plurality of external edges and the plurality of external surfaces comprise the electrically and thermally-conductive material, and
   wherein the probe head is configured to couple to a hand-held, thermo-electro-stimulation probe device configured to (a) selectively heat and cool the tip configured to cause the plurality of external surfaces and the plurality of external edges to selectively be warm and to selectively be cold to respectively heat and cool an individual's skin and (b) provide electro-stimulation to the individual's skin through the tip.

\* \* \* \* \*